US007704717B2

(12) United States Patent
Cahoon et al.

(10) Patent No.: US 7,704,717 B2
(45) Date of Patent: Apr. 27, 2010

(54) PLANT CAFFEIC ACID-3-O-METHYLTRANSFERASE HOMOLOGS

(75) Inventors: Rebecca E. Cahoon, Lincoln, NE (US); J. Antoni Rafalski, Wilmington, DE (US); Jennie B. Shen, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/012,352

(22) Filed: Feb. 1, 2008

(65) Prior Publication Data

US 2008/0166731 A1 Jul. 10, 2008

Related U.S. Application Data

(62) Division of application No. 11/515,174, filed on Sep. 1, 2006, now Pat. No. 7,351,565, which is a division of application No. 10/464,610, filed on Jun. 17, 2003, now Pat. No. 7,129,088, which is a division of application No. 09/971,823, filed on Oct. 5, 2001, now Pat. No. 6,610,521, which is a division of application No. 09/500,569, filed on Feb. 9, 2000, now Pat. No. 6,329,204.

(60) Provisional application No. 60/119,587, filed on Feb. 10, 1999.

(51) Int. Cl.

| | |
|---|---|
| ***C12N 9/00*** | (2006.01) |
| ***C12N 9/10*** | (2006.01) |
| ***C12N 5/02*** | (2006.01) |
| ***C12N 15/82*** | (2006.01) |
| ***C07H 21/04*** | (2006.01) |
| ***A01H 5/00*** | (2006.01) |

(52) U.S. Cl. ...................... 435/193; 435/183; 435/410; 435/468; 536/23.2; 800/278; 800/298

(58) Field of Classification Search ...................... None
See application file for complete search history.

(56) References Cited

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Vance et al., "Lignification as a Mechanism of Disease Resistance", Ann Rev Phytopathol., 1980, vol. 18:259-288.
Kentaro Inoue et al., "Developmental Expression and Substrate Specifities of Alfalfa Caffeic Acid . . . ", Plant Physiol, 1998, vol. 117:761-770.
Upendra N. Dwivedi et al., "Modification Of Lignin Biosynthesis In Transgenic Nicotiana . . . ", Plant Mol. Bio., vol. 26:61-71, 1994.
Alain M. Boudet et al., "Lignin Genetic Engineering", Mol. Breeding, vol. 2:25-39, 1996.
Malcolm M. Campbell et al, "Variation In Lignin Content And Composition", Plant Phys., vol. 110-3:3-13, 1996.
National Center For Biotechnology Information General Identifier No. 729135 (Dec. 5, 1998).
Pablo collazo et al., Structure And Expression Of The Lignin O-Methyltransferase Gene From *Zea mays* L., Plant Mol. Bio., 20:857-867 (1992).
National Center For Biotechnology Information General Identifier No. 116908 (Feb. 1, 1996).
Ganesan Gowri et al., Stress Responses In Alfalfa (*Medicago sativa* L.), Plant Phys., 1991, vol. 97:7-14.
National Center For Biotechnology Information General Identifier No. 1582580 (Oct. 28, 1996).
C.L. McIntyre et al., Sequence And Expression Of A Caffeic Acid O-Methyl Transferase . . . , Australian J Plant Physiol, vol. 22(3):471-478, 1995.
Karen Guzman et al., "The Gene Encoding Ovine Follicle-stimulating hormone B: Isolation . . . ", DNA And Cell Biology, vol. 10(8):593-601, 1991.
National Center For Biotechnology Information General Identifier No. 4104220 (Jan. 29, 1999).
National Center For Biotechnology Information General Identifier No. 6630734 (Dec. 21, 1999).
National Center For Biotechnology Information General Identifier No. 1314742 (Jun. 3, 1998).
J.E. Lee et al., "Genomic Sequence And Mapping Of A Methyljasmonate-Induced . . . ", DNA Sequence, vol. 7(6):357-363.
National Center For Biotechnology Information General Identifier No. 762870 (Apr. 14, 2000).
Toshio Hayakawa et al., "Molecular Cloning And Tissue-Specific Expression Of Two Genes . . . ", Plant Science, vol. 113:157-165, 1996.
National Center For Biotechnology Information General Identifier No. 542050 (Aug. 26, 1999).
Luca Pellegrini et al., "Molecular Cloning And Expression Of A New Class Of Ortho-Diphenol . . . ", Plant Physiol., vol. 103:509-517, 1993.
Ruiqin Zhon et al., "Essential Role Of Caffeoyl Coenzyme A O-Methyltransferase . . . ", Plant Physiol., vol. 124:563-577, Oct. 2000.

* cited by examiner

*Primary Examiner*—Christian L Fronda

(57) ABSTRACT

This invention relates to an isolated nucleic acid fragment encoding a protein involved in phenylpropanoid metabolism. The invention also relates to the construction of a chimeric gene encoding all or a portion of the protein involved in phenylpropanoid metabolism, in sense or antisense orientation, wherein expression of the chimeric gene results in production of altered levels of the protein involved in phenylpropanoid metabolism in a transformed host cell.

11 Claims, No Drawings

SEQUENCE LISTING

<160> NUMBER OF SEQ ID NOS: 28

<210> SEQ ID NO 1
<211> LENGTH: 1008
<212> TYPE: DNA
<213> ORGANISM: Oryza sativa
<220> FEATURE:
<221> NAME/KEY: unsure
<222> LOCATION: (522)
<223> OTHER INFORMATION: n = A, C, G or T

<400> SEQUENCE: 1
tgtatccagc ctcctcctcc ttcttctcca tcgccggcga gagagagaga gagttagcta 60
gctaggatgg gttctacagc cgccgacatg gccgcggcgg ccgacgagga ggcgtgcatg 120
tacgcgctgc agctggcgtc gtcgtcgatc ctgccgatga cgctcaagaa cgccatcgag 180
ctgggcctgc tcgagacgct gcagtccgcc gccgtcgccg gaggaggggg aaaggcggcg 240
ctgctgacgc cggcggaggt ggccgacaag ctgccgtcca aggcgaaccc ggcggcggcc 300
gacatggtgg accgcatgct ccgcctgctc gcctcctaca acgtcgtcag gtgcgagatg 360
gaggagggcg ccgacggcaa gctctcccgc cgctacgccg ccgcgccggt gtgcaagtgg 420
ctgacgccca acgaggacgg cgtctccatg gccgccctcg ccctcatgaa ccaggacaag 480
gtcctcatgg agagctggta ctaccttaag gacgcagctg gnaacggcgg catcccgttc 540
aacaaggcgt acgggatgac ggcgttcgag taccacggca cggacgcccg cttcaaccgc 600
gtcttcaacg agggcatgaa gaaccactcc gtcatcatca ccaagaagct gctcgacctc 660
tacaccggct tcgacgccgc ctccaccgtc gtcgacgtcg gcggcggcgt gggcgccact 720
gtggccgccg tcgtctcccg ccacccgcac atccgggggga tcaactacga cctcccccac 780
gtcatctccg aggcgccgcc gtttccccgg ggtggagcac gtcggcggcg acatgttcgc 840
ctccgtgccc cgcggcggcg aacgcaatcc tgatgaagtg gatcctccaa cgactggagc 900
gaacgagcac tgcgcgcggc tgctcaagaa ctgctacgaa cgcgctgccg gagcacggga 960
aggtggtggt ggtggagtgc gtgtgccgga gagcttccaa cgcgaagg 1008

<210> SEQ ID NO 2
<211> LENGTH: 305
<212> TYPE: PRT
<213> ORGANISM: Oryza sativa
<220> FEATURE:
<221> NAME/KEY: UNSURE
<222> LOCATION: (277)
<223> OTHER INFORMATION: Xaa = ANY AMINO ACID

<400> SEQUENCE: 2

Met Gly Ser Thr Ala Ala Asp Met Ala Ala Ala Ala Asp Glu Glu Ala
1 5 10 15

Cys Met Tyr Ala Leu Gln Leu Ala Ser Ser Ser Ile Leu Pro Met Thr
20 25 30

Leu Lys Asn Ala Ile Glu Leu Gly Leu Leu Glu Thr Leu Gln Ser Ala
35 40 45

Ala Val Ala Gly Gly Gly Gly Lys Ala Ala Leu Leu Thr Pro Ala Glu
50 55 60

Val Ala Asp Lys Leu Pro Ser Lys Ala Asn Pro Ala Ala Ala Asp Met
65 70 75 80

Val Asp Arg Met Leu Arg Leu Leu Ala Ser Tyr Asn Val Val Arg Cys
85 90 95

-continued

```
Glu Met Glu Glu Gly Ala Asp Gly Lys Leu Ser Arg Arg Tyr Ala Ala
            100                 105                 110

Ala Pro Val Cys Lys Trp Leu Thr Pro Asn Glu Asp Gly Val Ser Met
        115                 120                 125

Ala Ala Leu Ala Leu Met Asn Gln Asp Lys Val Leu Met Glu Ser Trp
    130                 135                 140

Tyr Tyr Leu Lys Asp Ala Ala Gly Asn Gly Gly Ile Pro Phe Asn Lys
145                 150                 155                 160

Ala Tyr Gly Met Thr Ala Phe Glu Tyr His Gly Thr Asp Ala Arg Phe
                165                 170                 175

Asn Arg Val Phe Asn Glu Gly Met Lys Asn His Ser Val Ile Ile Thr
            180                 185                 190

Lys Lys Leu Leu Asp Leu Tyr Thr Gly Phe Asp Ala Ala Ser Thr Val
        195                 200                 205

Val Asp Val Gly Gly Gly Val Gly Ala Thr Val Ala Ala Val Val Ser
    210                 215                 220

Arg His Pro His Ile Arg Gly Ile Asn Tyr Asp Leu Pro His Val Ile
225                 230                 235                 240

Ser Glu Ala Pro Pro Phe Pro Gly Val Glu His Val Gly Gly Asp Met
                245                 250                 255

Phe Ala Ser Val Pro Arg Gly Ala Asn Ala Ile Leu Met Lys Trp Ile
            260                 265                 270

Leu Gln Arg Leu Xaa Pro Asn Glu His Cys Ala Arg Leu Leu Lys Asn
        275                 280                 285

Cys Tyr Asp Ala Leu Pro Glu His Gly Lys Val Val Val Val Glu Cys
    290                 295                 300

Val
305


<210> SEQ ID NO 3
<211> LENGTH: 1370
<212> TYPE: DNA
<213> ORGANISM: Glycine max

<400> SEQUENCE: 3

gcacgagcac aagctcacag agcaagaaca ctgttccaat acggaatcta aggcaaagca      60

aaccaaacat cttgaatcat gggttcaaca ggtgagactc agattacccc aacccacgta     120

tctgatgaag aagcaaacct tttcgccatg caactagcca gtgcttctgt ccttccaatg     180

atcctcaaat cagcacttga gcttgatctg ttggaaatca tagccaaggc tggccctggt     240

gttcatcttt cccccactga catttcttct cagctcccaa cacagaaccc tgatgcaccc     300

gttatgttgg accgtatatt gcgcctattg gcttgctaca atatcctctc tttttctctc     360

cgcactctcc ctgatggcaa ggttgagagg ctctatggtc tcgcccccgt tgccaagtac     420

ttggttaaga acgaagatgg tgtctccatt gctgcgctca acctcatgaa ccaggacaaa     480

gtcctcatgg aaagctggta ctatttgaaa gatgcagtcc ttgaaggagg cattccattt     540

aacaaggctt atggaatgac agcctttgag taccatggaa cagatccaag gtttaacaag     600

gttttcaaca agggaatggc tgatcactct accatcacaa tgaagaaaat tcttgagacc     660

tacacaggtt ttgagagtct taaatctctg gttgatgttg gtggtgggac tggagctgta     720

atcaacatga ttgtctcaaa gcatcccact attaagggca ttaattttga tttgcctcat     780

gtcattgaag atgccccatc ttatcctgga gtggagcatg taggtggaga tatgtttgcg     840

agtgttccga aagctgatgc tatttttatg aagtggattt gccacgattg gagtgatgag     900
```

-continued

```
cactgcttga agtttttgaa gaactgctac gaggcactac cagacaatgg gaaggtgatt    960

gtggcagaat gcattcttcc agtggctcca gactctagct tggccacaaa aggtgtggtt   1020

cacatcgatg tgatcatgtt ggcacataat ccacgtggga aagagagaac agagaaagag   1080

tttgaggctc tggccaaagg gtctggattc caaggtttcc gagttgtttg ctgtgctttc   1140

aataccaaca tcatggaatt tctcaaaaag atttaagttc tttggcatgg attcatgtca   1200

agctgcattt gggttttgag attgaggttg tggttgtggt gctactttcc aaagctttcc   1260

cggaaaaacg taattttctc ttaggaaaag aataatgaac aagttcaatg tagactgcca   1320

atatcaaata acaagtttca ttttgtggat taaaaaaaaa aaaaaaaaaa              1370


<210> SEQ ID NO 4
<211> LENGTH: 365
<212> TYPE: PRT
<213> ORGANISM: Glycine max

<400> SEQUENCE: 4

Met Gly Ser Thr Gly Glu Thr Gln Ile Thr Pro Thr His Val Ser Asp
  1               5                  10                  15

Glu Glu Ala Asn Leu Phe Ala Met Gln Leu Ala Ser Ala Ser Val Leu
             20                  25                  30

Pro Met Ile Leu Lys Ser Ala Leu Glu Leu Asp Leu Leu Glu Ile Ile
         35                  40                  45

Ala Lys Ala Gly Pro Gly Val His Leu Ser Pro Thr Asp Ile Ser Ser
     50                  55                  60

Gln Leu Pro Thr Gln Asn Pro Asp Ala Pro Val Met Leu Asp Arg Ile
 65                  70                  75                  80

Leu Arg Leu Leu Ala Cys Tyr Asn Ile Leu Ser Phe Ser Leu Arg Thr
                 85                  90                  95

Leu Pro Asp Gly Lys Val Glu Arg Leu Tyr Gly Leu Ala Pro Val Ala
            100                 105                 110

Lys Tyr Leu Val Lys Asn Glu Asp Gly Val Ser Ile Ala Ala Leu Asn
        115                 120                 125

Leu Met Asn Gln Asp Lys Val Leu Met Glu Ser Trp Tyr Tyr Leu Lys
    130                 135                 140

Asp Ala Val Leu Glu Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
                165                 170                 175

Asn Lys Gly Met Ala Asp His Ser Thr Ile Thr Met Lys Lys Ile Leu
            180                 185                 190

Glu Thr Tyr Thr Gly Phe Glu Ser Leu Lys Ser Leu Val Asp Val Gly
        195                 200                 205

Gly Gly Thr Gly Ala Val Ile Asn Met Ile Val Ser Lys His Pro Thr
    210                 215                 220

Ile Lys Gly Ile Asn Phe Asp Leu Pro His Val Ile Glu Asp Ala Pro
225                 230                 235                 240

Ser Tyr Pro Gly Val Glu His Val Gly Gly Asp Met Phe Ala Ser Val
                245                 250                 255
```

-continued

```
Pro Lys Ala Asp Ala Ile Phe Met Lys Trp Ile Cys His Asp Trp Ser
            260                 265                 270

Asp Glu His Cys Leu Lys Phe Leu Lys Asn Cys Tyr Glu Ala Leu Pro
        275                 280                 285

Asp Asn Gly Lys Val Ile Val Ala Glu Cys Ile Leu Pro Val Ala Pro
    290                 295                 300

Asp Ser Ser Leu Ala Thr Lys Gly Val Val His Ile Asp Val Ile Met
305                 310                 315                 320

Leu Ala His Asn Pro Arg Gly Lys Glu Arg Thr Glu Lys Glu Phe Glu
                325                 330                 335

Ala Leu Ala Lys Gly Ser Gly Phe Gln Gly Phe Arg Val Val Cys Cys
            340                 345                 350

Ala Phe Asn Thr Asn Ile Met Glu Phe Leu Lys Lys Ile
        355                 360                 365


<210> SEQ ID NO 5
<211> LENGTH: 1314
<212> TYPE: DNA
<213> ORGANISM: Triticum aestivum

<400> SEQUENCE: 5

caaacatggg ctccaccgca gccgacatgg ccgcctccgc cgacgaggag gcgtgcatgt      60

atgctctcca gctcgtctcg tcgtcgatcc tcccgatgac gctcaagaac gccatcgagc     120

tgggtctcct ggagaccctg gtggccgccg gcggcaagct gctgacgccc gccgaggtgg     180

cagccaagct cccgtccacg gcgaatcccg ccgcggcgga catggtggac cgcatgctcc     240

ggctgctggc ctcgtacaac gtggtgtcgt gcacgatgga ggagggcaag gacggccggc     300

tgtcccggcg gtacggcgcc gcgcccgtgt gcaagttcct cacccccaac gaagacggcg     360

tctccatggc ggcgctcgcg ctcatgaacc aggacaaggt cctcatggag agctggtact     420

acctgaagga cgcggtcctt gacggcggca tcccgttcaa caaggcgtac gggatgtcgg     480

cgttcgagta ccacggcacg gacccgcgct tcaaccgcgt cttcaacgag gggatgaaga     540

accactccat catcatcacc aagaagctcc tcgaggtcta caagggcttc gagggcctcg     600

gcaccatcgt cgacgtgggc ggcggcgtgg gcgccatcgt cgccgcctac ccggccatca     660

agggcatcaa cttcgacctc ccccacgtca tctccgaggc gccaccgttc ccgggcgtca     720

cccacgtcgg cggcgacatg ttccagaagg tgccctcggg cgacgccatc ctcatgaagt     780

ggatcctcca cgactggagc gacgagcact gcgcgacgct gctcaagaac tgctacgacg     840

cgctgccggc gcacggcaag gtggtgctcg tggagtgcat cctgccggtg aacccggagg     900

ccacgcccaa ggcgcagggg gtattccacg tcgacatgat catgctcgcg cacaaccccg     960

gcggcaggga gaggtacgag agggagttcg aggccctggc caagggcgcc ggcttcaaag    1020

ccatcaagac cacctacatc tacgccaacg catttgccat cgagttcacc aagtagatcc    1080

atgccaaccg tccaccgctc gctttgagac catcttcttc ttcctcgctg gcgctgctga    1140

atatgtactt tggcttgctg tttcctctgt tttcctaatt ttgtcatcct agctctgaat    1200

cattctgaat gctactggtt gtgccgtcga tctacccatt cgaaatgtac tgtactatta    1260

atagtgctgc tcttaaaggt tgcatgtgat gcaatgaaaa aaaaaaaaaa aaaa          1314


<210> SEQ ID NO 6
<211> LENGTH: 356
<212> TYPE: PRT
<213> ORGANISM: Triticum aestivum
```

-continued

<400> SEQUENCE: 6

```
Met Gly Ser Thr Ala Ala Asp Met Ala Ala Ser Ala Asp Glu Glu Ala
  1               5                  10                  15

Cys Met Tyr Ala Leu Gln Leu Val Ser Ser Ser Ile Leu Pro Met Thr
             20                  25                  30

Leu Lys Asn Ala Ile Glu Leu Gly Leu Leu Glu Thr Leu Val Ala Ala
         35                  40                  45

Gly Gly Lys Leu Leu Thr Pro Ala Glu Val Ala Ala Lys Leu Pro Ser
     50                  55                  60

Thr Ala Asn Pro Ala Ala Ala Asp Met Val Asp Arg Met Leu Arg Leu
 65                  70                  75                  80

Leu Ala Ser Tyr Asn Val Val Ser Cys Thr Met Glu Glu Gly Lys Asp
                 85                  90                  95

Gly Arg Leu Ser Arg Arg Tyr Gly Ala Ala Pro Val Cys Lys Phe Leu
            100                 105                 110

Thr Pro Asn Glu Asp Gly Val Ser Met Ala Ala Leu Ala Leu Met Asn
        115                 120                 125

Gln Asp Lys Val Leu Met Glu Ser Trp Tyr Tyr Leu Lys Asp Ala Val
    130                 135                 140

Leu Asp Gly Gly Ile Pro Phe Asn Lys Ala Tyr Gly Met Ser Ala Phe
145                 150                 155                 160

Glu Tyr His Gly Thr Asp Pro Arg Phe Asn Arg Val Phe Asn Glu Gly
                165                 170                 175

Met Lys Asn His Ser Ile Ile Ile Thr Lys Lys Leu Leu Glu Val Tyr
            180                 185                 190

Lys Gly Phe Glu Gly Leu Gly Thr Ile Val Asp Val Gly Gly Gly Val
        195                 200                 205

Gly Ala Ile Val Ala Ala Tyr Pro Ala Ile Lys Gly Ile Asn Phe Asp
    210                 215                 220

Leu Pro His Val Ile Ser Glu Ala Pro Pro Phe Pro Gly Val Thr His
225                 230                 235                 240

Val Gly Gly Asp Met Phe Gln Lys Val Pro Ser Gly Asp Ala Ile Leu
                245                 250                 255

Met Lys Trp Ile Leu His Asp Trp Ser Asp Glu His Cys Ala Thr Leu
            260                 265                 270

Leu Lys Asn Cys Tyr Asp Ala Leu Pro Ala His Gly Lys Val Val Leu
        275                 280                 285

Val Glu Cys Ile Leu Pro Val Asn Pro Glu Ala Thr Pro Lys Ala Gln
    290                 295                 300

Gly Val Phe His Val Asp Met Ile Met Leu Ala His Asn Pro Gly Gly
305                 310                 315                 320

Arg Glu Arg Tyr Glu Arg Glu Phe Glu Ala Leu Ala Lys Gly Ala Gly
                325                 330                 335

Phe Lys Ala Ile Lys Thr Thr Tyr Ile Tyr Ala Asn Ala Phe Ala Ile
            340                 345                 350

Glu Phe Thr Lys
        355
```

<210> SEQ ID NO 7
<211> LENGTH: 760
<212> TYPE: DNA
<213> ORGANISM: Zea mays

-continued

<220> FEATURE:
<221> NAME/KEY: unsure
<222> LOCATION: (53)
<223> OTHER INFORMATION: n = A, C, G or T
<220> FEATURE:
<221> NAME/KEY: unsure
<222> LOCATION: (360)
<223> OTHER INFORMATION: n = A, C, G or T

<400> SEQUENCE: 7

```
cgggggtatc cgagcccctc atgggtgccc tcctcgacgg ctacggcgcc gcnggcgggt     60

ttcgcggcgt cgccacgctc gtagacgtcg ggggaagctc cggcgcctgc ctcgagatga    120

tcatgcgcag ggtccccaca atcaccgagg gcatcaactt cgacctcccc gacgtcgtcg    180

ccgcagcgcc gcccatcgcc ggagtgaggc atgttggcgg agatatgttc aagtccatcc    240

cctccggtga tgccattttc atgaagtggg ttctgacgac gtggaccgac gacgagtgca    300

cggccatcct gaggaactgc cacgccgctc tgccggacgg cggcaagctc gtggcctgcn    360

agccggtggt gccggaggag acggacagca gcaccaggac gagggcgctg ctggagaacg    420

acatcttcgt catgaccacc taccggacgc agggagggat gcgctccgag gaggagttcc    480

gccacctcgg cgtcgacgcc gcaggcttca ccgccttccg agccatctat ctcgacccct    540

tctatgccgt cctcgagtat accaagtgat ctccactcca tccgcccaaa tctccttgcg    600

agttgaatag cagaataacg aacagataaa taaagctatt ccattcacgt tggaatccga    660

atctctgcct actgtctgta ctcaacgtta gcttctgtaa ccaggatctc tctttcaagc    720

atttccaagc ttttgatgac aaaatcataa tttcgagctc                          760
```

<210> SEQ ID NO 8
<211> LENGTH: 188
<212> TYPE: PRT
<213> ORGANISM: Zea mays
<220> FEATURE:
<221> NAME/KEY: UNSURE
<222> LOCATION: (120)
<223> OTHER INFORMATION: Xaa = ANY AMINO ACID

<400> SEQUENCE: 8

```
Gly Val Ser Glu Pro Leu Met Gly Ala Leu Leu Asp Gly Tyr Gly Ala
  1               5                  10                  15

Ala Gly Gly Phe Arg Gly Val Ala Thr Leu Val Asp Val Gly Gly Ser
             20                  25                  30

Ser Gly Ala Cys Leu Glu Met Ile Met Arg Arg Val Pro Thr Ile Thr
         35                  40                  45

Glu Gly Ile Asn Phe Asp Leu Pro Asp Val Val Ala Ala Ala Pro Pro
     50                  55                  60

Ile Ala Gly Val Arg His Val Gly Gly Asp Met Phe Lys Ser Ile Pro
 65                  70                  75                  80

Ser Gly Asp Ala Ile Phe Met Lys Trp Val Leu Thr Thr Trp Thr Asp
                 85                  90                  95

Asp Glu Cys Thr Ala Ile Leu Arg Asn Cys His Ala Ala Leu Pro Asp
            100                 105                 110

Gly Gly Lys Leu Val Ala Cys Xaa Pro Val Val Pro Glu Glu Thr Asp
        115                 120                 125

Ser Ser Thr Arg Thr Arg Ala Leu Leu Glu Asn Asp Ile Phe Val Met
    130                 135                 140

Thr Thr Tyr Arg Thr Gln Gly Gly Met Arg Ser Glu Glu Glu Phe Arg
145                 150                 155                 160
```

-continued

```
His Leu Gly Val Asp Ala Ala Gly Phe Thr Ala Phe Arg Ala Ile Tyr
            165                 170                 175

Leu Asp Pro Phe Tyr Ala Val Leu Glu Tyr Thr Lys
        180                 185
```

<210> SEQ ID NO 9
<211> LENGTH: 1342
<212> TYPE: DNA
<213> ORGANISM: Oryza sativa

<400> SEQUENCE: 9

```
tagccatact gaccagagag gctcacatgg atccgtacac tagcagggct ccggcgagtg      60

gtggtgtcgc cgccggcgac gacgacgagg aggcggcgtg cctgcaggcg tttgagctaa     120

tgtgcatctt caccgtcccc atgacactga aggcggcgat cgagctcggc ctcctcgacg     180

cactagccgc cgccggcgac ggccgcgcac tgaccgcgga cgagctggcc gccgcgcggc     240

tcccggacgc ggcgccggac aaggccgagg cggcgtcctc ggtggaccgg atgctgcggc     300

tcctcgcgtc gttcgacgtc gtcaagtgct cgacggaggc cgggcccggc ggcgaacctc     360

cccggagacg atactcgccg gcgcccgtct gcaggttgtt caccgccggc ggcaacagcc     420

accgtggatc tctggccccc tcggtcttgt tcggcgtcga cgaggactac ctgtgcacct     480

ggcgtcagtt ggcggcggcg gtgggcggcg gcgggccgtc ggcgttcgag agggcgcacg     540

ggatgcggat gttcgagtac atggggacga accgccggct gaacacgctg ttcaaccagg     600

ccatggcgca gcagtccatg attgtgattg acaagctgct cgaccgcttc catgggttcg     660

acggcgtcgg cgtcctcgtc gacgtcggcg ggggcaccgg cgccaccctg gagatgatca     720

cctcccggta caagcatatc accggcgtta acttcgacct accccatgtc atctctcagg     780

ctccatctat tccgggtgtg aaacatatag ctggaaatat gtttgagagc atatctaata     840

ttggagatgc aattttctta aagatgatcc tccacatgca aaacgatgag gactgcatca     900

agatcctcaa gaattgccac caagccctgc cggacaatgg caaggtgatt gctgttgaga     960

ttgtcctccc gacgatccca gatctggccc aaacagcacg atacccgttc cagatggaca    1020

tgatcatgct cagcaattcc cggggaggaa aggagaggac agagctggag ttcgccaagc    1080

tagccacgga ctctggtttc agtggtgcct tgcgaacaac ctacatcttg gccaactatt    1140

gggttcttga gttcagcaag tagctctgaa aaatcatgtc aagttcaatt tgctaagcat    1200

tttaatgtgt gcatggttat ttcaatacca tacaaatggt gatcagaatc gctatatata    1260

ctgaacaata tatgtcaaat atacaatata aaatgtaaag tgtcccttaa aattgaaaaa    1320

aaaaaaaaaa aaaaaaaaaa aa                                             1342
```

<210> SEQ ID NO 10
<211> LENGTH: 378
<212> TYPE: PRT
<213> ORGANISM: Oryza sativa

<400> SEQUENCE: 10

```
Met Asp Pro Tyr Thr Ser Arg Ala Pro Ala Ser Gly Gly Val Ala Ala
  1               5                  10                  15

Gly Asp Asp Asp Glu Glu Ala Ala Cys Leu Gln Ala Phe Glu Leu Met
             20                  25                  30

Cys Ile Phe Thr Val Pro Met Thr Leu Lys Ala Ala Ile Glu Leu Gly
         35                  40                  45

Leu Leu Asp Ala Leu Ala Ala Ala Gly Asp Gly Arg Ala Leu Thr Ala
     50                  55                  60
```

-continued

```
Asp Glu Leu Ala Ala Ala Arg Leu Pro Asp Ala Ala Pro Asp Lys Ala
 65                  70                  75                  80

Glu Ala Ala Ser Ser Val Asp Arg Met Leu Arg Leu Leu Ala Ser Phe
                85                  90                  95

Asp Val Val Lys Cys Ser Thr Glu Ala Gly Pro Gly Gly Glu Pro Pro
            100                 105                 110

Arg Arg Arg Tyr Ser Pro Ala Pro Val Cys Arg Leu Phe Thr Ala Gly
        115                 120                 125

Gly Asn Ser His Arg Gly Ser Leu Ala Pro Ser Val Leu Phe Gly Val
    130                 135                 140

Asp Glu Asp Tyr Leu Cys Thr Trp Arg Gln Leu Ala Ala Ala Val Gly
145                 150                 155                 160

Gly Gly Gly Pro Ser Ala Phe Glu Arg Ala His Gly Met Arg Met Phe
                165                 170                 175

Glu Tyr Met Gly Thr Asn Arg Arg Leu Asn Thr Leu Phe Asn Gln Ala
            180                 185                 190

Met Ala Gln Gln Ser Met Ile Val Ile Asp Lys Leu Leu Asp Arg Phe
        195                 200                 205

His Gly Phe Asp Gly Val Gly Val Leu Val Asp Val Gly Gly Gly Thr
    210                 215                 220

Gly Ala Thr Leu Glu Met Ile Thr Ser Arg Tyr Lys His Ile Thr Gly
225                 230                 235                 240

Val Asn Phe Asp Leu Pro His Val Ile Ser Gln Ala Pro Ser Ile Pro
                245                 250                 255

Gly Val Lys His Ile Ala Gly Asn Met Phe Glu Ser Ile Ser Asn Ile
            260                 265                 270

Gly Asp Ala Ile Phe Leu Lys Met Ile Leu His Met Gln Asn Asp Glu
        275                 280                 285

Asp Cys Ile Lys Ile Leu Lys Asn Cys His Gln Ala Leu Pro Asp Asn
    290                 295                 300

Gly Lys Val Ile Ala Val Glu Ile Val Leu Pro Thr Ile Pro Asp Leu
305                 310                 315                 320

Ala Gln Thr Ala Arg Tyr Pro Phe Gln Met Asp Met Ile Met Leu Ser
                325                 330                 335

Asn Ser Arg Gly Gly Lys Glu Arg Thr Glu Leu Glu Phe Ala Lys Leu
            340                 345                 350

Ala Thr Asp Ser Gly Phe Ser Gly Ala Leu Arg Thr Thr Tyr Ile Leu
        355                 360                 365

Ala Asn Tyr Trp Val Leu Glu Phe Ser Lys
    370                 375


<210> SEQ ID NO 11
<211> LENGTH: 1195
<212> TYPE: DNA
<213> ORGANISM: Glycine max

<400> SEQUENCE: 11

gcacgagcat atcagtgata caaaagacaa gtaagaataa tcaagcaaga agaaatggaa      60

gaagaaaaaa gcttcaccta tgcaatgcag ctggtgaact ctagcgtgct atccatggcc     120

atgcactcag ccatagagct tggcattttt gacatcatag ccaaagcagg tgaaggtgcc     180

aaattatctg ccaaggacat tgcagccaag cttccatgca agaattcaga aggagccaca     240

atgttggatc gtatcctaag gctcctagta tgtcactcca tcattgactg cacagtggtt     300

gctgatcaac aacatggtcc tcctccacat ctgcaacggt tctatgccat gaaccctgtg     360
```

-continued

```
gccaaatact ttgcttccat tgatggtgct ggctcactag gccctttgat ggtcttgact    420

caggacaagg ccctccttca tagttggtac caattgaaag atgcaattct agaaggaggt    480

attcctttca acagggttca tggaaaacac gtgtttgaat attccgacat gaactcgagc    540

ttcaatcagc ttttcatggc agctatgaca aaccgtgcaa ctttaataat gaagaagatt    600

gttgaatcct acaaggggtt tgagcacctc aatagcctgg tggacgttgg aggtggcctt    660

ggtgtcacac ttaacatagt cacttctaaa taccctcaca ttaagggtat caattttgac    720

ttgccacatg tcatagaaca tgcctctacc tatcctggtg ttgagcatgt gggaggagat    780

atgtttgaaa gtgtgccaca aggagatgcc attttgatga tgtgtgtact tcatgattgg    840

agtgatgaat ggtgcttgaa ggtattaaag aattgttatg cttctattcc tagtgatgga    900

aaggtgattg ttgtggatgg aattcttcca tttgaaccaa agacaacagg tgcatcaaag    960

agcatttccc aatttgatgt actgatgatg actacaaacc caggagggaa ggagcgaagt   1020

gaagaggaat tcatggcatt ggcaaaagga gctggataca gtggcattag attcacatgc   1080

tttgtctctg acttatgggt tatggagttc ttcaagtaaa tgttgtatgt cacacatgct   1140

gctgcagatg gaataaaatg aaattagaaa ttgcaataaa aaaaaaaaaa aaaaa        1195
```

<210> SEQ ID NO 12
<211> LENGTH: 354
<212> TYPE: PRT
<213> ORGANISM: Glycine max

<400> SEQUENCE: 12

```
Met Glu Glu Glu Lys Ser Phe Thr Tyr Ala Met Gln Leu Val Asn Ser
  1               5                  10                  15

Ser Val Leu Ser Met Ala Met His Ser Ala Ile Glu Leu Gly Ile Phe
             20                  25                  30

Asp Ile Ile Ala Lys Ala Gly Glu Gly Ala Lys Leu Ser Ala Lys Asp
         35                  40                  45

Ile Ala Ala Lys Leu Pro Cys Lys Asn Ser Glu Gly Ala Thr Met Leu
     50                  55                  60

Asp Arg Ile Leu Arg Leu Leu Val Cys His Ser Ile Ile Asp Cys Thr
 65                  70                  75                  80

Val Val Ala Asp Gln Gln His Gly Pro Pro Pro His Leu Gln Arg Phe
                 85                  90                  95

Tyr Ala Met Asn Pro Val Ala Lys Tyr Phe Ala Ser Ile Asp Gly Ala
            100                 105                 110

Gly Ser Leu Gly Pro Leu Met Val Leu Thr Gln Asp Lys Ala Leu Leu
        115                 120                 125

His Ser Trp Tyr Gln Leu Lys Asp Ala Ile Leu Glu Gly Gly Ile Pro
    130                 135                 140

Phe Asn Arg Val His Gly Lys His Val Phe Glu Tyr Ser Asp Met Asn
145                 150                 155                 160

Ser Ser Phe Asn Gln Leu Phe Met Ala Ala Met Thr Asn Arg Ala Thr
                165                 170                 175

Leu Ile Met Lys Lys Ile Val Glu Ser Tyr Lys Gly Phe Glu His Leu
            180                 185                 190

Asn Ser Leu Val Asp Val Gly Gly Gly Leu Gly Val Thr Leu Asn Ile
        195                 200                 205

Val Thr Ser Lys Tyr Pro His Ile Lys Gly Ile Asn Phe Asp Leu Pro
    210                 215                 220
```

-continued

```
His Val Ile Glu His Ala Ser Thr Tyr Pro Gly Val Glu His Val Gly
225                 230                 235                 240

Gly Asp Met Phe Glu Ser Val Pro Gln Gly Asp Ala Ile Leu Met Met
                245                 250                 255

Cys Val Leu His Asp Trp Ser Asp Glu Trp Cys Leu Lys Val Leu Lys
            260                 265                 270

Asn Cys Tyr Ala Ser Ile Pro Ser Asp Gly Lys Val Ile Val Val Asp
        275                 280                 285

Gly Ile Leu Pro Phe Glu Pro Lys Thr Thr Gly Ala Ser Lys Ser Ile
    290                 295                 300

Ser Gln Phe Asp Val Leu Met Met Thr Thr Asn Pro Gly Gly Lys Glu
305                 310                 315                 320

Arg Ser Glu Glu Glu Phe Met Ala Leu Ala Lys Gly Ala Gly Tyr Ser
                325                 330                 335

Gly Ile Arg Phe Thr Cys Phe Val Ser Asp Leu Trp Val Met Glu Phe
            340                 345                 350

Phe Lys


<210> SEQ ID NO 13
<211> LENGTH: 1308
<212> TYPE: DNA
<213> ORGANISM: Triticum aestivum

<400> SEQUENCE: 13

ctcgtgccga attcggcacg agacaactat cagcagcacc agctcggcta tctccaaagt     60

ccgaacaagc agttaatata attatctgct aaatgggctc cactgccgtg gagaaggtcg    120

ctgtcgccac tggcgacgag gaggcgtgca tgtacgcggt gaagcttgca gcggcatcta    180

tccttccaat gaccctcaag aacgccatcg agctgggcat gctcgagatc ctcgtgggtg    240

ccggcgggaa gatgttgtca ccttcagagg tggcagcgca gcttccgtcg aaggccaacc    300

cggaggcacc ggttatggtg gaccgcatgc tgcggctgct ggcatcgaac aacgtcgtgt    360

catgcgaggt ggaggaaggt aaggacggcc tcctcgcccg tcgatacggc cccgcgcccg    420

tgtgtaagtg gctcacaccc aacgaggacg gcgcatccat ggctgggctg ctcctcatga    480

cccacgacaa ggtcactatg gagagctggt attatttgaa ggacgtggcc cttgaaggcg    540

gccaaccatt ccacagggcg cacgggatga cggcgtacga gtacaacagc acagacccac    600

gcgctaactg cttgttcaac gaggccatgc ttaaccactc caccatcatc accaagaagc    660

tcctcgagtt ctacaggggc ttcgacaacg tcgagaccct cgtggatgtc gccggtggcg    720

ttggtgccac agcccacgcc atcacctcaa agtacccgca catcaagggg gtaaacttcg    780

atctcccgca tgtcatatcc gaggcgccgc cctaccctgg cgtgcagcac atcgccggtg    840

acatgttcaa gaaggtgccc tccggcgatg ctatcctcct gaagtggatc ctccacaact    900

ggaccgacga ttactgtatg actcttctga ggaactgcta cgatgcgttg cccatgaatg    960

gcaaggtggt catcgtggag ggcatcctgc cggtgaaacc agatgcaatg cccagcacgc   1020

agacgatgtt ccaggtcgac atgatgatgc tgctgcacac cgcaggcggc aaggagaggg   1080

aactgagcga atttgaagag ctagcgaagg gcgctgggtt cagcacagtc aagaccagct   1140

acatctacag caccgcatgg gtcattgagt tcgtcaaata gatcactcta atattttctt   1200

gcttctgctc ctagtatcgg aatatgtact tttgagcttc cttttcctgc tgtccttagc   1260

atctcatgta atgtatcacc tcgtgccgaa ttcggcacga gctggtgc                1308
```

-continued

<210> SEQ ID NO 14
<211> LENGTH: 362
<212> TYPE: PRT
<213> ORGANISM: Triticum aestivum

<400> SEQUENCE: 14

```
Met Gly Ser Thr Ala Val Glu Lys Val Ala Val Ala Thr Gly Asp Glu
  1               5                  10                  15

Glu Ala Cys Met Tyr Ala Val Lys Leu Ala Ala Ala Ser Ile Leu Pro
             20                  25                  30

Met Thr Leu Lys Asn Ala Ile Glu Leu Gly Met Leu Glu Ile Leu Val
         35                  40                  45

Gly Ala Gly Gly Lys Met Leu Ser Pro Ser Glu Val Ala Ala Gln Leu
     50                  55                  60

Pro Ser Lys Ala Asn Pro Glu Ala Pro Val Met Val Asp Arg Met Leu
 65                  70                  75                  80

Arg Leu Leu Ala Ser Asn Asn Val Val Ser Cys Glu Val Glu Glu Gly
                 85                  90                  95

Lys Asp Gly Leu Leu Ala Arg Arg Tyr Gly Pro Ala Pro Val Cys Lys
            100                 105                 110

Trp Leu Thr Pro Asn Glu Asp Gly Ala Ser Met Ala Gly Leu Leu Leu
        115                 120                 125

Met Thr His Asp Lys Val Thr Met Glu Ser Trp Tyr Tyr Leu Lys Asp
    130                 135                 140

Val Ala Leu Glu Gly Gly Gln Pro Phe His Arg Ala His Gly Met Thr
145                 150                 155                 160

Ala Tyr Glu Tyr Asn Ser Thr Asp Pro Arg Ala Asn Cys Leu Phe Asn
                165                 170                 175

Glu Ala Met Leu Asn His Ser Thr Ile Ile Thr Lys Lys Leu Leu Glu
            180                 185                 190

Phe Tyr Arg Gly Phe Asp Asn Val Glu Thr Leu Val Asp Val Ala Gly
        195                 200                 205

Gly Val Gly Ala Thr Ala His Ala Ile Thr Ser Lys Tyr Pro His Ile
    210                 215                 220

Lys Gly Val Asn Phe Asp Leu Pro His Val Ile Ser Glu Ala Pro Pro
225                 230                 235                 240

Tyr Pro Gly Val Gln His Ile Ala Gly Asp Met Phe Lys Lys Val Pro
                245                 250                 255

Ser Gly Asp Ala Ile Leu Leu Lys Trp Ile Leu His Asn Trp Thr Asp
            260                 265                 270

Asp Tyr Cys Met Thr Leu Leu Arg Asn Cys Tyr Asp Ala Leu Pro Met
        275                 280                 285

Asn Gly Lys Val Val Ile Val Glu Gly Ile Leu Pro Val Lys Pro Asp
    290                 295                 300

Ala Met Pro Ser Thr Gln Thr Met Phe Gln Val Asp Met Met Met Leu
305                 310                 315                 320

Leu His Thr Ala Gly Gly Lys Glu Arg Glu Leu Ser Glu Phe Glu Glu
                325                 330                 335

Leu Ala Lys Gly Ala Gly Phe Ser Thr Val Lys Thr Ser Tyr Ile Tyr
            340                 345                 350

Ser Thr Ala Trp Val Ile Glu Phe Val Lys
        355                 360
```

-continued

<210> SEQ ID NO 15
<211> LENGTH: 1458
<212> TYPE: DNA
<213> ORGANISM: Oryza sativa
<400> SEQUENCE: 15
gcacgaggtt taaacgtgcc atgtagtgca ccaacacgcc atatactagt ttcagaattg 60
agacacactg atcattgtga gagagaagta gaccaaacaa ggcaagctcg catggcttcg 120
ggcattagca ggactccggc cacgggtgtc accgccggcg gcggcgacga cgaggaggcg 180
gcatggttgc acgcgcttga gctgatctcg ggcttcaccg tctccatgac actgaaggcg 240
gcgatccagc tcggactcat cgacgcactt accgccgccg ccgacggccg cgcgctgacc 300
gccggcgagc tggttgcgca gctcccggcg gtggacgatg ccgaggcggc gacctcggtg 360
gaccggatgc tgcggctcct ggcgtcgttc aacgtcgtca ggtgctcgac ggaggcgggg 420
cctggcggtg atcctctccg gcgctactcg ccggcgcctg tgtgcaggtg gttcaccgcc 480
ggcgacaacc accaagggtc tctggcaccc aggctcatgc tcgacgtcga cgaagacaat 540
ctgagcacct ggcatcagat ggcggcggcg gtcgtcagcg gtgggccatc ggcgttcgag 600
agggcgcacg ggatgccatt gtttgagtac atggggacga accaccggtt caatatgctg 660
ttcaaccagg ccatgtcgca gcagtccatg atggtgatga acaagctgct agaccgcttc 720
catgggtttg atggcatcag tgtcctcgtc gacgtcggcg ggggcaccgg cgtcaccctg 780
aagatgatca tctcccggta taagcacatt actggtgtca acttcgactt accccacgtc 840
atatctcagg ctccatctct tccgggtgtg aatcatgtag ctggaaatat gtttgagagc 900
gtacctaaag gagatgcaat ttcttgaag tcgatgctcc tacgaaacga tgaggagtgc 960
atcaagattc tcaagaactg ccactatgct ctctcagaca atgggaaggt gattgttgtt 1020
gatattgttc tccctgaaac cccaaaaccg gtacccgaag cacaaaaccc actccggatg 1080
gacgttatga tgctcaacaa tcttcgtgga ggaaagataa ggacagagca ggagtacgcg 1140
aagctagcta tggattctgg cttcagtggt tccttccgga caacctacat tttcgccaac 1200
tttatggcaa ttgaactatg caagtagctc ttgaaaatca tgtcaagttc gtattactcc 1260
cttcatcact aactgaactt ttggctatgt atgtagacaa tcattttgct cagatatctt 1320
gtccatatgt acagccaaat gctcacgaag gagtatgtat ttcaatgtgt aattgtgtat 1380
ggctaacact ataccattca atggtctgaa aattaaaaac ttttcttcaa taataaaaaa 1440
aaaaaaaaaa aaaaaaaa 1458

<210> SEQ ID NO 16
<211> LENGTH: 371
<212> TYPE: PRT
<213> ORGANISM: Oryza sativa

<400> SEQUENCE: 16

Met Ala Ser Gly Ile Ser Arg Thr Pro Ala Thr Gly Val Thr Ala Gly
1 5 10 15

Gly Gly Asp Asp Glu Glu Ala Ala Trp Leu His Ala Leu Glu Leu Ile
20 25 30

Ser Gly Phe Thr Val Ser Met Thr Leu Lys Ala Ala Ile Gln Leu Gly
35 40 45

Leu Ile Asp Ala Leu Thr Ala Ala Ala Asp Gly Arg Ala Leu Thr Ala
50 55 60

Gly Glu Leu Val Ala Gln Leu Pro Ala Val Asp Asp Ala Glu Ala Ala
65 70 75 80

-continued

```
Thr Ser Val Asp Arg Met Leu Arg Leu Leu Ala Ser Phe Asn Val Val
                85                  90                  95

Arg Cys Ser Thr Glu Ala Gly Pro Gly Gly Asp Pro Leu Arg Arg Tyr
            100                 105                 110

Ser Pro Ala Pro Val Cys Arg Trp Phe Thr Ala Gly Asp Asn His Gln
        115                 120                 125

Gly Ser Leu Ala Pro Arg Leu Met Leu Asp Val Asp Glu Asp Asn Leu
    130                 135                 140

Ser Thr Trp His Gln Met Ala Ala Ala Val Val Ser Gly Gly Pro Ser
145                 150                 155                 160

Ala Phe Glu Arg Ala His Gly Met Pro Leu Phe Glu Tyr Met Gly Thr
                165                 170                 175

Asn His Arg Phe Asn Met Leu Phe Asn Gln Ala Met Ser Gln Gln Ser
            180                 185                 190

Met Met Val Met Asn Lys Leu Leu Asp Arg Phe His Gly Phe Asp Gly
        195                 200                 205

Ile Ser Val Leu Val Asp Val Gly Gly Gly Thr Gly Val Thr Leu Lys
    210                 215                 220

Met Ile Ile Ser Arg Tyr Lys His Ile Thr Gly Val Asn Phe Asp Leu
225                 230                 235                 240

Pro His Val Ile Ser Gln Ala Pro Ser Leu Pro Gly Val Asn His Val
                245                 250                 255

Ala Gly Asn Met Phe Glu Ser Val Pro Lys Gly Asp Ala Ile Phe Leu
            260                 265                 270

Lys Ser Met Leu Leu Arg Asn Asp Glu Glu Cys Ile Lys Ile Leu Lys
        275                 280                 285

Asn Cys His Tyr Ala Leu Ser Asp Asn Gly Lys Val Ile Val Val Asp
    290                 295                 300

Ile Val Leu Pro Glu Thr Pro Lys Pro Val Pro Glu Ala Gln Asn Pro
305                 310                 315                 320

Leu Arg Met Asp Val Met Met Leu Asn Asn Leu Arg Gly Gly Lys Ile
                325                 330                 335

Arg Thr Glu Gln Glu Tyr Ala Lys Leu Ala Met Asp Ser Gly Phe Ser
            340                 345                 350

Gly Ser Phe Arg Thr Thr Tyr Ile Phe Ala Asn Phe Met Ala Ile Glu
        355                 360                 365

Leu Cys Lys
    370
```

<210> SEQ ID NO 17
<211> LENGTH: 1314
<212> TYPE: DNA
<213> ORGANISM: Glycine max
<220> FEATURE:
<221> NAME/KEY: unsure
<222> LOCATION: (472)
<223> OTHER INFORMATION: n = A, C, G or T
<220> FEATURE:
<221> NAME/KEY: unsure
<222> LOCATION: (1156)
<223> OTHER INFORMATION: n = A, C, G or T
<220> FEATURE:
<221> NAME/KEY: unsure
<222> LOCATION: (1180)
<223> OTHER INFORMATION: n = A, C, G or T
<220> FEATURE:
<221> NAME/KEY: unsure
<222> LOCATION: (1262)
<223> OTHER INFORMATION: n = A, C, G or T -continued
<220> FEATURE:
<221> NAME/KEY: unsure
<222> LOCATION: (1302)
<223> OTHER INFORMATION: n = A, C, G or T

<400> SEQUENCE: 17
cacaagctca cagagcaaga acactgttcc aatacggaat ctaaggcaaa gcaaaccaaa 60
catcttgaat catgggttca acaggtgaga ctcagattac tccaacccat gtatctgatg 120
aagaggcaaa ccttttcgcc atgcaactag ccagtgcctc agtactccct atggttctca 180
aatcagctct tgagcttgat ctgttggaaa tcatagccaa ggctggccct ggtgttcacc 240 tttcccctc cgacattgct tctcggctcc caacacacaa ccctgatgca cccgttatgt 300
tggaccgtat attgcgcctc ttggcttgct acaatatcct ctctttttct cttcgcactc 360
tccctcatgg caaggttgag aggctctatg gtctcgcccc tgttgctaag tacttggtca 420
ggaacgaaga tggtgtctcc attgctgctc tcaacctcat gaaccaggac anaatcctca 480
tggaaagctg gtactatttg aaagatgcag tccttgaagg gggtattcca tttaacaaag 540
catatggaat gacagccttt gaataccatg gaacggatcc aaggtttaac aaggttttca 600
acaaggggat ggctgatcac tctaccatta caatgaagaa aattcttgag acctacacag 660
gctttgaggg acttaaatcc ctggttgatg ttggtggagg aactggagct gtagtcaaca 720
tgattgtctc aaagtatccc actattaagg gcattaattt tgatttgccc catgtcattg 780
aagatgcccc atcttatcca ggagtggaac atgttggtgg agatatgttt gtcagtgttc 840
caaaagctga tgctattttt atgaagtgga tttgccacga ttggagtgat gagcactgct 900
tgaagttttt gaagaactgc tatgaggcac taccagataa tgggaaagtg attgtggcgg 960
aatgcattct tccggtggct ccagactcta gcttggccac aaagggtgtg gttcacatcg 1020
atgtgatcat gttggctcac aatccaggtg gggaaagaga gaacaagaga aagagtttga 1080
ggctctgggc caaaggctct ggattccaag gtttccaagt ccctgtgctg tgctttcaat 1140
acctaccgtc aatggnaatt tctcaaaaaa gggtttaagn tcttttggcg tggattcata 1200
atcaaagttg caatttggga ttttgacttt tgagactccg gcttgggggt gctaacctta 1260
cnaaatggtt ttccccggga aaaacttaaa tttcttccaa angccttatg aaaa 1314

<210> SEQ ID NO 18
<211> LENGTH: 358
<212> TYPE: PRT
<213> ORGANISM: Glycine max
<220> FEATURE:
<221> NAME/KEY: UNSURE
<222> LOCATION: (134)
<223> OTHER INFORMATION: Xaa = ANY AMINO ACID

<400> SEQUENCE: 18

Met Gly Ser Thr Gly Glu Thr Gln Ile Thr Pro Thr His Val Ser Asp
1 5 10 15

Glu Glu Ala Asn Leu Phe Ala Met Gln Leu Ala Ser Ala Ser Val Leu
20 25 30

Pro Met Val Leu Lys Ser Ala Leu Glu Leu Asp Leu Leu Glu Ile Ile
35 40 45

Ala Lys Ala Gly Pro Gly Val His Leu Ser Pro Ser Asp Ile Ala Ser
50 55 60

Arg Leu Pro Thr His Asn Pro Asp Ala Pro Val Met Leu Asp Arg Ile
65 70 75 80

-continued

```
Leu Arg Leu Leu Ala Cys Tyr Asn Ile Leu Ser Phe Ser Leu Arg Thr
                 85                  90                  95

Leu Pro His Gly Lys Val Glu Arg Leu Tyr Gly Leu Ala Pro Val Ala
            100                 105                 110

Lys Tyr Leu Val Arg Asn Glu Asp Gly Val Ser Ile Ala Ala Leu Asn
        115                 120                 125

Leu Met Asn Gln Asp Xaa Ile Leu Met Glu Ser Trp Tyr Tyr Leu Lys
    130                 135                 140

Asp Ala Val Leu Glu Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
                165                 170                 175

Asn Lys Gly Met Ala Asp His Ser Thr Ile Thr Met Lys Lys Ile Leu
            180                 185                 190

Glu Thr Tyr Thr Gly Phe Glu Gly Leu Lys Ser Leu Val Asp Val Gly
        195                 200                 205

Gly Gly Thr Gly Ala Val Val Asn Met Ile Val Ser Lys Tyr Pro Thr
    210                 215                 220

Ile Lys Gly Ile Asn Phe Asp Leu Pro His Val Ile Glu Asp Ala Pro
225                 230                 235                 240

Ser Tyr Pro Gly Val Glu His Val Gly Gly Asp Met Phe Val Ser Val
                245                 250                 255

Pro Lys Ala Asp Ala Ile Phe Met Lys Trp Ile Cys His Asp Trp Ser
            260                 265                 270

Asp Glu His Cys Leu Lys Phe Leu Lys Asn Cys Tyr Glu Ala Leu Pro
        275                 280                 285

Asp Asn Gly Lys Val Ile Val Ala Glu Cys Ile Leu Pro Val Ala Pro
    290                 295                 300

Asp Ser Ser Leu Ala Thr Lys Gly Val Val His Ile Asp Val Ile Met
305                 310                 315                 320

Leu Ala His Asn Pro Gly Gly Glu Arg Glu Asn Lys Arg Lys Ser Leu
                325                 330                 335

Arg Leu Trp Ala Lys Gly Ser Gly Phe Gln Gly Phe Gln Val Leu Cys
            340                 345                 350

Cys Ala Phe Asn Thr Tyr
        355
```

<210> SEQ ID NO 19
<211> LENGTH: 926
<212> TYPE: DNA
<213> ORGANISM: Triticum aestivum
<220> FEATURE:
<221> NAME/KEY: unsure
<222> LOCATION: (627)..(628)
<223> OTHER INFORMATION: n = A, C, G or T
<220> FEATURE:
<221> NAME/KEY: unsure
<222> LOCATION: (806)
<223> OTHER INFORMATION: n = A, C, G or T
<220> FEATURE:
<221> NAME/KEY: unsure
<222> LOCATION: (836)
<223> OTHER INFORMATION: n = A, C, G or T
<220> FEATURE:
<221> NAME/KEY: unsure
<222> LOCATION: (848)
<223> OTHER INFORMATION: n = A, C, G or T -continued
<220> FEATURE:
<221> NAME/KEY: unsure
<222> LOCATION: (857)
<223> OTHER INFORMATION: n = A, C, G or T
<220> FEATURE:
<221> NAME/KEY: unsure
<222> LOCATION: (863)
<223> OTHER INFORMATION: n = A, C, G or T
<220> FEATURE:
<221> NAME/KEY: unsure
<222> LOCATION: (866)
<223> OTHER INFORMATION: n = A, C, G or T
<220> FEATURE:
<221> NAME/KEY: unsure
<222> LOCATION: (871)
<223> OTHER INFORMATION: n = A, C, G or T
<220> FEATURE:
<221> NAME/KEY: unsure
<222> LOCATION: (884)
<223> OTHER INFORMATION: n = A, C, G or T
<220> FEATURE:
<221> NAME/KEY: unsure
<222> LOCATION: (891)
<223> OTHER INFORMATION: n = A, C, G or T
<220> FEATURE:
<221> NAME/KEY: unsure
<222> LOCATION: (905)
<223> OTHER INFORMATION: n = A, C, G or T
<220> FEATURE:
<221> NAME/KEY: unsure
<222> LOCATION: (917)
<223> OTHER INFORMATION: n = A, C, G or T

<400> SEQUENCE: 19
aacatgggct ccaccgcagc cgacatggcc gcctccgccg acgaggaggc gtgcatgtat 60
gctctccagc tcgtctcgtc gtcgatcctc ccgatgacgc tcaagaacgc catcgagctg 120
ggtctcctgg agaccctggt ggccgccggc ggcaagctgc tgacgcccgc cgaggtggca 180
gccaagctcc cgtccacggc gaatcccgcc gcggcggaca tggtggaccg catgctccgg 240
ctgctggcct cgtacaacgt ggtgtcgtgc acgatggagg agggcaagga cggccggctg 300
tcccggcggt acggcgccgc gcccgtgtgc aagttcctca cccccaacga agacggcgtc 360
tccatggcgg cgctcgcgct catgaaccag gacaaggtcc tcatggagag ctggtactac 420
ctgaaggacg cggtccttga cggcggcatc ccgttcaaca aggcgtacgg gatgtcggcg 480
ttcgagtacc acggcacgga cccgcgcttc aaccgcgtct tcaacgaggg gatgaagaac 540
cactccatca tcatcaccaa gaagctcctc gaggtctaca agggcttcga gggcctcggc 600
accatcgtca gtttgggccg gcgcgtnngg cgccatcgtc gccgcctacc cggccatcaa 660
gggcatcaac ttcgacctcc cccacgtcat ctccgaaggc gccaccgttc ccgggcgtca 720
ccacgtcggc ggcgaatttc cagaaggtgc ctccgggcga cgccatcctc atgagtgggg 780
ttctccaacg actgggagcg acgaanaact gcgcgacgct gctcaaagaa tgtacnaagc 840
ctgccggnga aggaagntgg ggnccntgga ntgaactgcg ggtnaaccgg nggcaaccca 900
aggcnagggg attcaantca aattta 926

<210> SEQ ID NO 20
<211> LENGTH: 231
<212> TYPE: PRT
<213> ORGANISM: Triticum aestivum
<220> FEATURE:
<221> NAME/KEY: UNSURE
<222> LOCATION: (208)
<223> OTHER INFORMATION: Xaa = ANY AMINO ACID -continued

<400> SEQUENCE: 20

```
Met Gly Ser Thr Ala Ala Asp Met Ala Ala Ser Ala Asp Glu Glu Ala
  1               5                  10                  15

Cys Met Tyr Ala Leu Gln Leu Val Ser Ser Ser Ile Leu Pro Met Thr
             20                  25                  30

Leu Lys Asn Ala Ile Glu Leu Gly Leu Leu Glu Thr Leu Val Ala Ala
         35                  40                  45

Gly Gly Lys Leu Leu Thr Pro Ala Glu Val Ala Ala Lys Leu Pro Ser
     50                  55                  60

Thr Ala Asn Pro Ala Ala Ala Asp Met Val Asp Arg Met Leu Arg Leu
 65                  70                  75                  80

Leu Ala Ser Tyr Asn Val Val Ser Cys Thr Met Glu Glu Gly Lys Asp
                 85                  90                  95

Gly Arg Leu Ser Arg Arg Tyr Gly Ala Ala Pro Val Cys Lys Phe Leu
            100                 105                 110

Thr Pro Asn Glu Asp Gly Val Ser Met Ala Ala Leu Ala Leu Met Asn
        115                 120                 125

Gln Asp Lys Val Leu Met Glu Ser Trp Tyr Tyr Leu Lys Asp Ala Val
    130                 135                 140

Leu Asp Gly Gly Ile Pro Phe Asn Lys Ala Tyr Gly Met Ser Ala Phe
145                 150                 155                 160

Glu Tyr His Gly Thr Asp Pro Arg Phe Asn Arg Val Phe Asn Glu Gly
                165                 170                 175

Met Lys Asn His Ser Ile Ile Ile Thr Lys Lys Leu Leu Glu Val Tyr
            180                 185                 190

Lys Gly Phe Glu Gly Leu Gly Thr Ile Val Ser Leu Ala Gly Ala Xaa
        195                 200                 205

Gly Ala Ile Val Ala Ala Tyr Pro Ala Ile Lys Gly Ile Asn Phe Asp
    210                 215                 220

Leu Pro His Val Ile Ser Glu
225                 230
```

<210> SEQ ID NO 21
<211> LENGTH: 603
<212> TYPE: DNA
<213> ORGANISM: Oryza sativa
<220> FEATURE:
<221> NAME/KEY: unsure
<222> LOCATION: (506)
<223> OTHER INFORMATION: n = A, C, G or T
<220> FEATURE:
<221> NAME/KEY: unsure
<222> LOCATION: (508)
<223> OTHER INFORMATION: n = A, C, G or T
<220> FEATURE:
<221> NAME/KEY: unsure
<222> LOCATION: (511)
<223> OTHER INFORMATION: n = A, C, G or T
<220> FEATURE:
<221> NAME/KEY: unsure
<222> LOCATION: (529)
<223> OTHER INFORMATION: n = A, C, G or T
<220> FEATURE:
<221> NAME/KEY: unsure
<222> LOCATION: (531)
<223> OTHER INFORMATION: n = A, C, G or T
<220> FEATURE:
<221> NAME/KEY: unsure
<222> LOCATION: (554)
<223> OTHER INFORMATION: n = A, C, G or T -continued
<220> FEATURE:
<221> NAME/KEY: unsure
<222> LOCATION: (577)..(578)
<223> OTHER INFORMATION: n = A, C, G or T

<400> SEQUENCE: 21
gccatactga ccagagaggc tcacatggat ccgtacacta gcagggctcc ggcgagtggt 60
ggtgtcgccg ccggcgacga cgacgaggag gcggcgtgcc tgcaggcgtt tgagctaatg 120
tgcatcttca ccgtccccat gacactgaag gcggcgatcg agctcggcct cctcgacgca 180
ctagccgccg ccggcgacgg ccgcgcactg accgcggacg agctggccgc cgcgcggctc 240
ccggacgcgg cgccggacaa ggccgaggcg gcgtcctcgg tggaccggat gctgcggctc 300
ctcgcgtcgt tcgacgtcgt caagtgctcg acggaggccg ggcccggcgg cgaacctccc 360
cgggagacga tactcgccgg cgcccgtctg caagttgttc accgccggcg gcaacagcca 420
ccgtggatct ctggcccccct cggtcttgtt cggcgtcgac gaggactacc tgtgcactgg 480
cgtagttggc ggcggcggtg ggccgncngc nggccgtcgg cgttcgaana nggccaacgg 540
gatccggatg ttcnagtaca tgggaacaaa cgccggnnga aaccggtcaa caagcaatgg 600
cga 603

<210> SEQ ID NO 22
<211> LENGTH: 109
<212> TYPE: PRT
<213> ORGANISM: Oryza sativa

<400> SEQUENCE: 22

Met Asp Pro Tyr Thr Ser Arg Ala Pro Ala Ser Gly Gly Val Ala Ala
1 5 10 15

Gly Asp Asp Asp Glu Glu Ala Ala Cys Leu Gln Ala Phe Glu Leu Met
20 25 30

Cys Ile Phe Thr Val Pro Met Thr Leu Lys Ala Ala Ile Glu Leu Gly
35 40 45

Leu Leu Asp Ala Leu Ala Ala Ala Gly Asp Gly Arg Ala Leu Thr Ala
50 55 60

Asp Glu Leu Ala Ala Ala Arg Leu Pro Asp Ala Ala Pro Asp Lys Ala
65 70 75 80

Glu Ala Ala Ser Ser Val Asp Arg Met Leu Arg Leu Leu Ala Ser Phe
85 90 95

Asp Val Val Lys Cys Ser Thr Glu Ala Gly Pro Gly Gly
100 105

<210> SEQ ID NO 23
<211> LENGTH: 511
<212> TYPE: DNA
<213> ORGANISM: Glycine max
<220> FEATURE:
<221> NAME/KEY: unsure
<222> LOCATION: (264)
<223> OTHER INFORMATION: n = A, C, G or T
<220> FEATURE:
<221> NAME/KEY: unsure
<222> LOCATION: (355)
<223> OTHER INFORMATION: n = A, C, G or T
<220> FEATURE:
<221> NAME/KEY: unsure
<222> LOCATION: (386)
<223> OTHER INFORMATION: n = A, C, G or T
<220> FEATURE:
<221> NAME/KEY: unsure
<222> LOCATION: (408)
<223> OTHER INFORMATION: n = A, C, G or T -continued
<220> FEATURE:
<221> NAME/KEY: unsure
<222> LOCATION: (435)
<223> OTHER INFORMATION: n = A, C, G or T
<220> FEATURE:
<221> NAME/KEY: unsure
<222> LOCATION: (475)..(476)
<223> OTHER INFORMATION: n = A, C, G or T

<400> SEQUENCE: 23
catatcagtg atacaaaaga caagtaagaa taatcaagca agaagaaatg gaagaagaaa 60
aaagcttcac ctatgcaatg cagctggtga actctagcgt gctatccatg gccatgcact 120
cagccataga gcttggcatt tttgacatca tagccaaagc aggtgaaggt gccaaattat 180
ctgccaagga cattgcagcc aagcttccat gcaagaattc agaaggagcc acaatgttgg 240
atcgtatcct aaggctccta gtangtcact ccatcattga ctgcacagtg gttgctgatc 300
aacaacatgg tcctcctcca catctgcaac ggttctatgc catgaaccct gtggncaaat 360
actttgcttc cattgatggt gctggntcac taagcccttt gatggtcntt gactcaagac 420
aagggcctcc ttcanagttt ggtaccaatt gaaagatgca attctagaaa gaggnnttcc 480
cttcaacaag ggttcaaggg aaacacgtgt t 511

<210> SEQ ID NO 24
<211> LENGTH: 82
<212> TYPE: PRT
<213> ORGANISM: Glycine max
<220> FEATURE:
<221> NAME/KEY: UNSURE
<222> LOCATION: (74)
<223> OTHER INFORMATION: Xaa = ANY AMINO ACID

<400> SEQUENCE: 24

Glu Met Glu Glu Glu Lys Ser Phe Thr Tyr Ala Met Gln Leu Val Asn
1 5 10 15

Ser Ser Val Leu Ser Met Ala Met His Ser Ala Ile Glu Leu Gly Ile
20 25 30

Phe Asp Ile Ile Ala Lys Ala Gly Glu Gly Ala Lys Leu Ser Ala Lys
35 40 45

Asp Ile Ala Ala Lys Leu Pro Cys Lys Asn Ser Glu Gly Ala Thr Met
50 55 60

Leu Asp Arg Ile Leu Arg Leu Leu Val Xaa His Ser Ile Ile Asp Cys
65 70 75 80

Thr Val

<210> SEQ ID NO 25
<211> LENGTH: 849
<212> TYPE: DNA
<213> ORGANISM: Triticum aestivum
<220> FEATURE:
<221> NAME/KEY: unsure
<222> LOCATION: (9)
<223> OTHER INFORMATION: n = A, C, G or T
<220> FEATURE:
<221> NAME/KEY: unsure
<222> LOCATION: (11)
<223> OTHER INFORMATION: n = A, C, G or T
<220> FEATURE:
<221> NAME/KEY: unsure
<222> LOCATION: (22)
<223> OTHER INFORMATION: n = A, C, G or T
<220> FEATURE:
<221> NAME/KEY: unsure
<222> LOCATION: (44)
<223> OTHER INFORMATION: n = A, C, G or T -continued
<220> FEATURE:
<221> NAME/KEY: unsure
<222> LOCATION: (56)
<223> OTHER INFORMATION: n = A, C, G or T
<220> FEATURE:
<221> NAME/KEY: unsure
<222> LOCATION: (58)..(59)
<223> OTHER INFORMATION: n = A, C, G or T
<220> FEATURE:
<221> NAME/KEY: unsure
<222> LOCATION: (73)
<223> OTHER INFORMATION: n = A, C, G or T
<220> FEATURE:
<221> NAME/KEY: unsure
<222> LOCATION: (94)
<223> OTHER INFORMATION: n = A, C, G or T
<220> FEATURE:
<221> NAME/KEY: unsure
<222> LOCATION: (120)
<223> OTHER INFORMATION: n = A, C, G or T
<220> FEATURE:
<221> NAME/KEY: unsure
<222> LOCATION: (133)
<223> OTHER INFORMATION: n = A, C, G or T
<220> FEATURE:
<221> NAME/KEY: unsure
<222> LOCATION: (153)
<223> OTHER INFORMATION: n = A, C, G or T
<220> FEATURE:
<221> NAME/KEY: unsure
<222> LOCATION: (155)
<223> OTHER INFORMATION: n = A, C, G or T
<220> FEATURE:
<221> NAME/KEY: unsure
<222> LOCATION: (164)
<223> OTHER INFORMATION: n = A, C, G or T
<220> FEATURE:
<221> NAME/KEY: unsure
<222> LOCATION: (170)
<223> OTHER INFORMATION: n = A, C, G or T
<220> FEATURE:
<221> NAME/KEY: unsure
<222> LOCATION: (188)
<223> OTHER INFORMATION: n = A, C, G or T
<220> FEATURE:
<221> NAME/KEY: unsure
<222> LOCATION: (190)
<223> OTHER INFORMATION: n = A, C, G or T
<220> FEATURE:
<221> NAME/KEY: unsure
<222> LOCATION: (235)
<223> OTHER INFORMATION: n = A, C, G or T
<220> FEATURE:
<221> NAME/KEY: unsure
<222> LOCATION: (253)
<223> OTHER INFORMATION: n = A, C, G or T
<220> FEATURE:
<221> NAME/KEY: unsure
<222> LOCATION: (277)
<223> OTHER INFORMATION: n = A, C, G or T
<220> FEATURE:
<221> NAME/KEY: unsure
<222> LOCATION: (297)
<223> OTHER INFORMATION: n = A, C, G or T
<220> FEATURE:
<221> NAME/KEY: unsure
<222> LOCATION: (406)
<223> OTHER INFORMATION: n = A, C, G or T

<400> SEQUENCE: 25
gaagcccgnc ngtttagtgc cncccagggg agccaccatg ttgntgtcct ataccnanna 60
ggtctttggg gantgtttta ttgaggaggt gccnttgagg ggccacccat tccacagggn 120

-continued

```
gacgggttac ggntagatac acacacaacc cangngttaa ttgnttgttn acggaggcca    180

tgttacantn ccccccatca tcaccaagaa gctcctcgat ttctacaggg gcttngacaa    240

cgtcgagacc ctngttgatg tcgccggtgg cgttgtncca cagcccacgc catcacntca    300

aagtacccgc acatcaaggg ggtaaacttc gatctcccgc atgtcatatc cgaggcgccg    360

cccttacctg gcgtgcagca catcgccggt gacatgttca agaagntgcc ctccggcgat    420

gctatcctcc tgaagtggat cctccacaac tggaccgacg attactgtat gactcttctg    480

aggaactgct acgatgcgtt gcccatgaat ggcaaggtgg tcatcgtgga gggcatcctg    540

ccggtgaaac cagatgcaat gcccagcacg cagacgatgt tccaggtcga catgatgatg    600

ctgctgcaca ccgcaggcgg caaggagagg gaactgagcg aatttgaaga gctagcgaag    660

ggcgctgggt tcagcagtca agaccagcta catctacagc accgcatggt cattgagttc    720

gtcaaataga tcactctaat attttcttgc ttctgctcct agtatcggaa tatgtacttt    780

tgagcttcct tttcctgctg tccttagcat ctcatgtaat gtatcacctc gtgccgaatt    840

cggcacgag                                                            849
```

```
<210> SEQ ID NO 26
<211> LENGTH: 174
<212> TYPE: PRT
<213> ORGANISM: Triticum aestivum
<220> FEATURE:
<221> NAME/KEY: UNSURE
<222> LOCATION: (13)
<223> OTHER INFORMATION: Xaa = ANY AMINO ACID
<220> FEATURE:
<221> NAME/KEY: UNSURE
<222> LOCATION: (27)..(28)
<223> OTHER INFORMATION: Xaa = ANY AMINO ACID
<220> FEATURE:
<221> NAME/KEY: UNSURE
<222> LOCATION: (71)
<223> OTHER INFORMATION: Xaa = ANY AMINO ACID

<400> SEQUENCE: 26

Ile Ile Thr Lys Lys Leu Leu Asp Phe Tyr Arg Gly Xaa Asp Asn Val
  1               5                  10                  15

Glu Thr Leu Val Asp Val Ala Gly Gly Val Xaa Xaa Thr Ala His Ala
             20                  25                  30

Ile Thr Ser Lys Tyr Pro His Ile Lys Gly Val Asn Phe Asp Leu Pro
         35                  40                  45

His Val Ile Ser Glu Ala Pro Pro Leu Pro Gly Val Gln His Ile Ala
     50                  55                  60

Gly Asp Met Phe Lys Lys Xaa Pro Ser Gly Asp Ala Ile Leu Leu Lys
 65                  70                  75                  80

Trp Ile Leu His Asn Trp Thr Asp Asp Tyr Cys Met Thr Leu Leu Arg
                 85                  90                  95

Asn Cys Tyr Asp Ala Leu Pro Met Asn Gly Lys Val Val Ile Val Glu
            100                 105                 110

Gly Ile Leu Pro Val Lys Pro Asp Ala Met Pro Ser Thr Gln Thr Met
        115                 120                 125

Phe Gln Val Asp Met Met Met Leu Leu His Thr Ala Gly Gly Lys Glu
    130                 135                 140

Arg Glu Leu Ser Glu Phe Glu Glu Leu Ala Lys Gly Ala Gly Phe Ser
145                 150                 155                 160

Ala Val Lys Thr Ser Tyr Ile Tyr Ser Thr Ala Trp Ser Leu
                165                 170
```

<210> SEQ ID NO 27
<211> LENGTH: 627
<212> TYPE: DNA
<213> ORGANISM: Oryza sativa
<220> FEATURE:
<221> NAME/KEY: unsure
<222> LOCATION: (404)
<223> OTHER INFORMATION: n = A, C, G or T
<220> FEATURE:
<221> NAME/KEY: unsure
<222> LOCATION: (457)
<223> OTHER INFORMATION: n = A, C, G or T
<220> FEATURE:
<221> NAME/KEY: unsure
<222> LOCATION: (465)
<223> OTHER INFORMATION: n = A, C, G or T
<220> FEATURE:
<221> NAME/KEY: unsure
<222> LOCATION: (488)
<223> OTHER INFORMATION: n = A, C, G or T
<220> FEATURE:
<221> NAME/KEY: unsure
<222> LOCATION: (500)
<223> OTHER INFORMATION: n = A, C, G or T
<220> FEATURE:
<221> NAME/KEY: unsure
<222> LOCATION: (524)
<223> OTHER INFORMATION: n = A, C, G or T
<220> FEATURE:
<221> NAME/KEY: unsure
<222> LOCATION: (553)
<223> OTHER INFORMATION: n = A, C, G or T
<220> FEATURE:
<221> NAME/KEY: unsure
<222> LOCATION: (567)
<223> OTHER INFORMATION: n = A, C, G or T
<220> FEATURE:
<221> NAME/KEY: unsure
<222> LOCATION: (598)
<223> OTHER INFORMATION: n = A, C, G or T
<220> FEATURE:
<221> NAME/KEY: unsure
<222> LOCATION: (604)
<223> OTHER INFORMATION: n = A, C, G or T
<220> FEATURE:
<221> NAME/KEY: unsure
<222> LOCATION: (607)
<223> OTHER INFORMATION: n = A, C, G or T
<220> FEATURE:
<221> NAME/KEY: unsure
<222> LOCATION: (613)
<223> OTHER INFORMATION: n = A, C, G or T

<400> SEQUENCE: 27
gtttaaacgt gccatgtagt gcaccaacac gccatatact agtttcagaa ttgagacaca 60
ctgatcattg tgagagagaa gtagaccaaa caaggcaagc tcgcatggct tcgggcatta 120
gcaggactcc ggccacgggt gtcaccgccg gcggcggcga cgacgaggag gcggcatggt 180
tgcacgcgct tgagctgatc tcgggcttca ccgtctccat gacactgaag gcggcgatcc 240
agctcggact catcgacgca cttaccgccg ccgccgacgg ccgcgcgctg accgccggcg 300
agcgggttgc gcagctcccg gcggtggacg atgccgaggc ggcgacctcg gtggaccgga 360
tgctgcggct cctggcgtcg ttcaacgtcg tcaggtgctc gacngaggcg gggcctggcg 420
gtgatcctct ccggcgctac tcgccggcgc ctgtgtncaa gtggntcacc gccggggaca 480
accacaangg tctctggcan ccaagctcat gctcgacttc gacnaagaca tctgagcact 540
ggcatcaaat ggnggcgggg gtcgtancgg tgggcatcgg cttccaaaag gccacgtnat 600
gaanaantgc tanacgctcc atggttt 627

-continued

```
<210> SEQ ID NO 28
<211> LENGTH: 123
<212> TYPE: PRT
<213> ORGANISM: Oryza sativa
<220> FEATURE:
<221> NAME/KEY: UNSURE
<222> LOCATION: (118)
<223> OTHER INFORMATION: Xaa = ANY AMINO ACID
<220> FEATURE:
<221> NAME/KEY: UNSURE
<222> LOCATION: (121)
<223> OTHER INFORMATION: Xaa = ANY AMINO ACID

<400> SEQUENCE: 28

Met Ala Ser Gly Ile Ser Arg Thr Pro Ala Thr Gly Val Thr Ala Gly
  1               5                  10                  15

Gly Gly Asp Asp Glu Glu Ala Ala Trp Leu His Ala Leu Glu Leu Ile
             20                  25                  30

Ser Gly Phe Thr Val Ser Met Thr Leu Lys Ala Ala Ile Gln Leu Gly
         35                  40                  45

Leu Ile Asp Ala Leu Thr Ala Ala Ala Asp Gly Arg Ala Leu Thr Ala
     50                  55                  60

Gly Glu Arg Val Ala Gln Leu Pro Ala Val Asp Asp Ala Glu Ala Ala
 65                  70                  75                  80

Thr Ser Val Asp Arg Met Leu Arg Leu Leu Ala Ser Phe Asn Val Val
                 85                  90                  95

Arg Cys Ser Thr Glu Ala Gly Pro Gly Gly Asp Pro Leu Arg Arg Tyr
            100                 105                 110

Ser Pro Ala Pro Val Xaa Lys Trp Xaa Thr Ala
        115                 120
```

PLANT CAFFEIC ACID-3-O-METHYLTRANSFERASE HOMOLOGS

This application claims the benefit of U.S. Provisional Application No. 60/119,587, filed Feb. 10, 1999.

FIELD OF THE INVENTION

This invention is in the field of plant molecular biology. More specifically, this invention pertains to nucleic acid fragments encoding proteins involved in phenylpropanoid metabolism in plants and seeds.

BACKGROUND OF THE INVENTION

Plant cells and tissues can respond to mechanical, chemical or pathogen induced injury by producing various phenolic compounds including mono- or dimethoxylated lignin precursors derived from cinnamic acid via a complex series of biochemical reactions. These lignin precursors are eventually used by the plant to produce the lignin polymer which helps in wound repair by adding hydrophobicity, a physical barrier against pathogen infection and mechanical strength to the injured tissue (Vance, C. P., et al., 1980, *Annu Rev Phytopathol* 18:259-288). Biosynthesis of the mono- or dimethoxylated lignin precursors occures, in part, by the action of two enzymes, caffeic acid 3-O-methyltransferase (COMT), also known as caffeic acid/5-hydroxyferulic acid O-methyltransferase and caffeoyl CoA 3-O-methyltransferase (CCOMT). Both enzymes have been isolated and purified from a wide variety of plant species.

Studies have shown that the activities of COMT and CCOMT increase prior to lignin deposition (Inoue, K., et al., 1998, *Plant Physiol* 117(3):761-770). Synthesis of lignin precursors involves the methylation of caffeic acid to yield ferulic acid followed by 5-hydroxylation of ferulate then a second methyltion to yield sinapate. COMT has been implicated in the methylation of both caffeic acid and 5-hydroxyferulic acid ((Inoue, K., et al., 1998, *Plant Physiol* 117(3):761-770). Research indicates that COM transcripts are present at high levels in organs containing vascular tissue and one study suggests that antisense inhibition of COMT can lead to modified lignin content and composition in the xylem and phloem of transgenic plant tissue (Dwivedi, U., et al., 1994, *Plant Mol. Biol.* 26:61-71).

Because of lignins importance in cell wall architecture and wound repair mechanisms there is considerable interest in the prospects for altering lignin quantity or quality by genetic engineering. For example, chemical treatments needed to remove lignin during the paper-pulping process are expensive and environmentally unfriendly. Plants with altered lignin quantity or quality could benefit this industry (Boudet, A., et al., 1996, *Mol Breeding* 2:25-39; Campbell, M., et al., 1996, *Plant Physiol* 110:3-13). Thus, there is a great deal of interest in identifying the genes that encode proteins involved in the production of lignin in plants. These genes may be used in plant cells to control lignin production. Accordingly, the availability of nucleic acid sequences encoding all or a portion of an enzyme involved in the production of lignin would facilitate studies to better understand lignin production in plant cells and provide genetic tools to enhance or otherwise alter lignin biosynthesis which in turn could provide mechanisms to control cell wall architecture and host defence and injury repair mechanisms in plant cells.

SUMMARY OF THE INVENTION

The present invention relates to isolated polynucleotides comprising a nucleotide sequence encoding a polypeptide of at least 305 amino acids that has at least 92% identity based on the Clustal method of alignment when compared to a polypeptide selected from the group consisting of a corn caffeic acid 3-O-methyltransferase polypeptide of SEQ ID NO:8, rice caffeic acid 3-O-methyltransferase polypeptides of SEQ ID NOs:2, 10 and 16, soybean caffeic acid 3-O-methyltransferase polypeptides of SEQ ID NOs:4 and 12, and wheat caffeic acid 3-O-methyltransferase polypeptides of SEQ ID NOs:6 and 14. The present invention also relates to an isolated polynucleotide comprising the complement of the nucleotide sequences described above.

The present invention relates to isolated polynucleotides comprising a nucleotide sequence encoding a polypeptide of at least 50 amino acids that has at least 80% identity based on the Clustal method of alignment when compared to a polypeptide selected from the group consisting of SEQ ID NOs:18, 20, 22, 24 and 28. The present invention also relates to an isolated polynucleotide comprising the complement of the nucleotide sequences described above.

It is preferred that the isolated polynucleotides of the claimed invention consists of a nucleic acid sequence selected from the group consisting of SEQ ID NOs:1, 3, 5, 7, 9, 11, 13, 15, 17, 19, 21, 23, 25 and 27 that codes for the polypeptide selected from the group consisting of SEQ ID NOs:2, 4, 6, 8, 10, 12, 14, 16, 18, 20, 22, 24, 26, and 28. The present invention also relates to an isolated polynucleotide comprising a nucleotide sequences of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a caffeic acid 3-O-methyltransferase polypeptide of at least 305 amino acids comprising at least 92% homology based on the Clustal method of alignment compared to a polypeptide selected from the group consisting of SEQ ID NOs:2, 4, 6, 8, 10, 12, 14 and 16.

The present invention relates to a method of selecting an isolated polynucleotide that affects the level of expression of a caffeic acid 3-O-methyltransferase polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a caffeic acid 3-O-methyltransferase polypeptide in the host cell containing the isolated polynucleotide; and (d) comparing the level of a caffeic acid 3-O-methyltransferase polypeptide in the host cell containing the isolated polynucleotide with the level of a caffeic acid 3-O-methyltransferase polypeptide in the host cell that does not contain the isolated polynucleotide.

The present invention relates to a method of obtaining a nucleic acid fragment encoding a substantial portion of a caffeic acid 3-O-methyltransferase polypeptide gene, preferably a plant caffeic acid 3-O-methyltransferase polypeptide gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27 and the complement of such nucleotide sequences; and amplifying a nucleic acid fragment (preferably a cDNA inserted in a cloning vector) using the oligonucleotide primer. The amplified nucleic acid fragment preferably will encode a portion of a caffeic acid 3-O-methyltransferase amino acid sequence.

The present invention also relates to a method of obtaining a nucleic acid fragment encoding all or a substantial portion of the amino acid sequence encoding a caffeic acid 3-O-methyltransferase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

The present invention relates to a composition, such as a hybridization mixture, comprising an isolated polynucleotide of the present invention.

The present invention relates to an isolated polynucleotide of the present invention comprising at least one of 30 contiguous nucleotides derived from a nucleic acid sequence selected from the group consisting of SEQ ID NOs:1, 3, 5, 7, 9, 11, 13, 15, 17, 19, 21, 23, 25 and 27.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the caffeic acid 3-O-methyltransferase polynucleotide in an amount sufficient to complement a null mutant and alter methylation of both caffeic acid and 5-hydroxyferulic acid to provide a positive selection means.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide sequences, SEQ ID NOs:3, 5, 9, 11, 13 and 15 and amino acid sequences SEQ ID NOs:4, 6, 10, 12, 14 and 16 were determined by further sequence analysis of cDNA clones encoding the amino acid sequences set forth in SEQ ID NOs:4, 6, 10, 12, 14 and 16. Nucleotide SEQ ID NOs:1, 17, 19, 21, 23, 25 and 27 and amino acid SEQ ID NOs:2, 18, 20, 22, 24, 26 and 28 were presented in a U.S. Provisional Application No. 60/119,587, filed Feb. 10, 1999.

The sequence descriptions and Sequence Listing attached hereto comply with the rules governing nucleotide and/or amino acid sequence disclosures in patent applications as set forth in 37 C.F.R. §1.821-1.825.

TABLE 1

Proteins Involved in Phenylpropanoid Metabolism

| Protein | Clone Designation | SEQ ID NO: (Nucleotide) | SEQ ID NO: (Amino Acid) |
|---|---|---|---|
| Caffeic acid 3-O-methyltransferase | Contig composed of:<br>rl0n.pk084.c19<br>rls48.pk0011.d2<br>rr1.pk0011.a10<br>rsl1n.pk001.c5 | 1 | 2 |
| Caffeic acid 3-O-methyltransferase | se2.27d08 CGS | 3 | 4 |
| Caffeic acid 3-O-methyltransferase | wlm96.pk033.c5 CGS | 5 | 6 |
| Caffeic acid 3-O-methyltransferase | Contig composed of:<br>cpg1c.pk016.m11<br>crln.pk0031.e3<br>p0092.chwaj20r | 7 | 8 |
| Caffeic acid 3-O-methyltransferase | rlr24.pk0094.b11 CGS | 9 | 10 |
| Caffeic acid 3-O-methyltransferase | srr3c.pk002.h5 CGS | 11 | 12 |
| Caffeic acid 3-O-methyltransferase | wlm96.pk025.c3 CGS | 13 | 14 |
| Caffeic acid 3-O-methyltransferase | rlr6.pk0035.a3 CGS | 15 | 16 |
| Caffeic acid 3-O-methyltransferase | Contig composed of:<br>se2.27d08<br>se4.12b11<br>srr1c.pk002.o15<br>ssl.pk0036.g7 | 17 | 18 |
| Caffeic acid 3-O-methyltransferase | Contig composed of:<br>wdk9n.pk001.h14<br>wlk4.pk0009.2<br>wlm96.pk033.c5 | 19 | 20 |
| Caffeic acid 3-O-methyltransferase | Contig composed of:<br>rlr24.pk0094.b11<br>rr1.pk083.n7<br>rsr9n.pk005.d1 | 21 | 22 |
| Caffeic acid 3-O-methyltransferase | srr3c.pk002.h5 EST | 23 | 24 |
| Caffeic acid 3-O-methyltransferase | Contig composed of:<br>wlm96.pk025.c3<br>wlm96.pk034.p19<br>wlm96.pk038.f14 | 25 | 26 |
| Caffeic acid 3-O-methyltransferase | Contig composed of:<br>rl0n.pk0018.e3<br>rl0n.pk0071.f10<br>rlr6.pk0035.a3<br>rls48.pk0008.f12<br>rsr9n.pk003.i18 | 27 | 28 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, 19, 21, 23, 25, 27 or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantiallv similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27 and the complement of such nucleotide sequences may be used in methods of selecting an isolated polynucleotide that affects the expression of a polypeptide (caffeic acid 3-O-methyltransferase) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transonic organisms in amounts or proportions that differ from that of normal or non-transformed organisms.

"Mature" protein refers to a post-translationally processed polypeptide; i.e., one from which any pre- or propeptides present in the primary translation product have been removed.

"Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth Enzymol.* 143:277) and particle-accelerated or "gene gun" transformation technology (Klein et al. (1987) *Nature* (London) 327:70-73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several proteins involved in phenylpropanoid metabolism have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other caffeic acid 3-O-methyltransferase proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as caffeic acid 3-O-methyltransferase) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide (caffeic acid 3-O-methyltransferase).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of methylation of both caffeic acid and 5-hydroxyferulic acid in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100: 1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded phenylpropanoid metabolism protein. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:3741. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin Med* 11:95-96), polymorphism of PCR-amplified fragments (CAPS; Sheffield et al. (1993) *Genomics* 16:325-332), allele-specific ligation (Landegren et al. (11988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Balinger and Benzer (1989) *Proc. Natl. Acad. Sci. USA* 86:9402-9406; Koes et al. (1995) *Proc. Natl. Acad Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor.

With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

TABLE 2 cDNA Libraries from Corn, Rice, Soybean and Wheat

| Library | Tissue | Clone |
|---|---|---|
| cpg1c | Corn pooled BMS treated with chemicals related to RNA, DNA synthesis** | cpg1c.pk016.m11 |
| cr1n | Corn Root From 7 Day Old Seedlings* | cr1n.pk0031.e3 |
| p0092 | Corn Husks* | p0092.chwaj20r |
| rl0n | Rice 15 Day Old Leaf* | rl0n.pk0018.e3<br>rl0n.pk084.c19<br>rl0n.pk0071.f10 |
| rlr6 | Rice Leaf 15 Days After Germination, 6 Hours After Infection of Strain *Magaporthe grisea* 4360-R-62 (AVR2-YAMO); Resistant | rlr6.pk0035.a3 |
| rlr24 | Rice Leaf 15 Days After Germination, 24 Hours After Infection of Strain *Magaporthe grisea* 4360-R-62 (AVR2-YAMO); Resistant | rlr24.pk0094.b11 |
| rls48 | Rice Leaf 15 Days After Germination, 48 Hours After Infection of Strain *Magaporthe grisea* 4360-R-67 (AVR2-YAMO); Susceptible | rls48.pk0008.f12<br>rls48.pk0011.d2 |
| rr1 | Rice Root of Two Week Old Developing Seedling | rr1.pk0011.a10<br>rr1.pk083.n7 |
| rsr9n | Rice Leaf 15 Days After Germination Harvested 2-72 Hours Following Infection With *Magnaporta grisea* (4360-R-62 and 4360-R-67)* | rsr9n.pk003.i18<br>rsr9n.pk005.d1 |
| rsl1n | Rice 15-Day-Old Seedling* | rsl1n.pk001.c5 |
| se2 | Soybean Embryo, 13 Days After Flowering | se2.27d08 |
| se4 | Soybean Embryo, 19 Days After Flowering | se4.12b11 |
| srr3c | Soybean 8-Day-Old Root | srr3c.pk002.h5 |
| srr1c | Soybean 8-Day-Old Root | srr1c.pk002.o15 |
| ss1 | Soybean Seedling 5-10 Days After Germination | ss1.pk0036.g7 |
| wlk4 | Wheat Seedlings 4 Hours After Treatment With fungicide*** | wlk4.pk0009.e2 |
| wdk9n | Wheat Kernels 3, 7, 14 and 21 Days After Anthesis | wdk9n.pk001.h14 |
| wlm96 | Wheat Seedlings 96 Hours After Inoculation With *Erysiphe graminis f.* sp *tritici* | wlm96.pk025.c3<br>wlm96.pk034.p19<br>wlm96.pk033.c5<br>wlm96.pk038.f14 |

*These libraries were normalized essentially as described in U.S. Pat. No. 5,482,845, incorporated herein by reference.
**Chemicals used included hydroxyurea, aphidicolin, HC-toxin, actinomysin D
***Fungicide Application of 6-iodo-2-propoxy-3-propyl-4(3H)-quinazolinone; synthesis and methods of using this compound are described in USSN 08/545,827, incorporated herein by reference.

Example 2

Identification of cDNA Clones cDNA clones encoding caffeic acid 3-O-methyltransferase proteins were identified by conducting BLAST (Basic Local Alignment Search Tool; Altschul et al. (1993) *J. Mol. Biol.* 215:403-410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Caffeic Acid 3-O-methyltransferase

The BLASTX search using the EST sequences from clones listed in Table 3 revealed similarity of the polypeptides encoded by the cDNAs to caffeic acid 3-O-methyltransferase from *Zea mays* (NCBI Identifier No. gi 729135), *Medicago sativa* (NCBI Identifier No. gi 116908), *Stylosanthes humilis* (NCBI Identifier No. gi 1582580), *Lolium perenne* (NCBI Identifier No. gi 2388664), *Lolium perenne* (NCBI Identifier No. gi 4104220), *Arabidopsis thaliana* (NCBI Identifier No. gi 6630734), *Hordeum vulgare* (NCBI Identifier No. gi 1314742), *Populus kitakamiensis* (NCBI Identifier No. gi 762870) and *Populus kitakamiensis* (NCBI Identifier No. gi 542050). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to *Zea mays, Medicago sativa, Stylosanthes humilis, Lolium perenne, Arabidopsis thaliana, Hordeum vulgare, Populus kitakamiensis* and *Populus kitakamiensis* Caffeic Acid 3-O-methyltransferase

| Clone | Status | BLAST pLog Score |
|---|---|---|
| Contig composed of:<br>rl0n.pk084.c19<br>rls48.pk0011.d2<br>rr1.pk0011.a10<br>rsl1n.pk001.c5 | Contig | 134.00 (gi 729135) |

TABLE 3-continued

BLAST Results for Sequences Encoding Polypeptides Homologous to *Zea mays, Medicago sativa, Stylosanthes humilis, Lolium perenne, Arabidopsis thaliana, Hordeum vulgare, Populus kitakamiensis* and *Populus kitakamiensis* Caffeic Acid 3-O-methyltransferase

| Clone | Status | BLAST pLog Score |
|---|---|---|
| se2.27d08 | CGS | >254.00 (gi 152580) |
| wlm96.pk033.c5 | CGS | >254.00 (gi 4104220) |
| Contig composed of:<br>cpg1c.pk016.m11<br>cr1n.pk0031.e3<br>p0092.chwaj20r | Contig | 72.52 (gi 6630734) |
| rlr24.pk0094.b11 | CGS | 103.00 (gi 1314742) |
| srr3c.pk002.h5 | CGS | 115.00 (gi 542050) |
| wlm96.pk025.c3 | CGS | 147.00 (gi 4104220) |
| rlr6.pk0035.a3 | CGS | 101.00 (gi 1314742) |

TABLE 4

Percent Identity of Amino Acid Sequences Deduced From the Nucleotide Sequences of cDNA Clones Encoding Polypeptides Homologous to *Zea mays, Medicago sativa, Stylosanthes humilis, Lolium perenne, Arabidopsis thaliana, Hordeum vulgare, Populus kitakamiensis* and *Populus kitakamiensis* Caffeic Acid 3-O-methyltransferase

| SEQ ID NO. | Percent Identity to |
|---|---|
| 2 | 74% (gi 729135) |
| 4 | 90% (gi 1582580) |
| 6 | 89% (gi 4104220) |
| 8 | 62% (gi 6630734) |
| 10 | 48% (gi 1314742) |
| 12 | 52% (gi 542050) |
| 14 | 69% (gi 4104220) |
| 16 | 47% (gi 1314742) |

The data in Table 4 represents a calculation of the percent identity of the amino acid sequences set forth in SEQ ID NOs:2, 4, 6, 8, 10, 12, 14 and 16 and the *Zea mays, Medicaao sativa, Stylosanthes humilis, Loliumperenne, Arabidopsis thaliana, Hordeum vulgare, Populus kitakamiensis* and *Populus kitakamiensis* sequences. The percent identity between the SEQ ID NOs ranged from 25% to 90%.

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a caffeic acid 3-O-methyltransferase. These sequences represent the first corn, rice, soybean and wheat sequences encoding caffeic acid 3-O-methyltransferase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL 1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μmL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These call may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS 1000/HE instrument (helium retrofit) can be used or these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. Coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Various modifications of the invention in addition to those shown and described herein will be apparent to those skilled in the art from the foregoing description. Such modifications are also intended to fall within the scope of the appended claims.

The disclosure of each reference set forth, above is incorporated herein by reference in its entirety.

What is claimed is:

1. An isolated polynucleotide comprising:

(a) a nucleotide sequence encoding a polypeptide having the activity of caffeic acid 3-O-methyltransferase, wherein the amino acid sequence of the polypeptide and the amino acid sequence of SEQ ID NO:16 have at least 95% sequence identity based on the Clustal alignment method, or (b) the complement of the nucleotide sequence.

2. The polynucleotide of claim 1, wherein the nucleotide sequence comprises the nucleotide sequence of SEQ ID NO:15.

3. The polynucleotide of claim 1, wherein the polypeptide comprises the amino acid sequence of SEQ ID NO:16.

4. A vector comprising the polynucleotide of claim 1.

5. A recombinant DNA construct comprising the polynucleotide of claim 1 operably linked to a regulatory sequence.

6. A method for transforming a cell comprising transforming a cell with the recombinant DNA construct of claim 5.

7. A host cell comprising the recombinant DNA construct of claim 5.

8. A method for producing a plant comprising transforming a plant cell with the recombinant DNA construct of claim 5 and regenerating a plant from the transformed plant cell.

9. A plant comprising the recombinant DNA construct of claim 5.

10. A seed comprising the recombinant DNA construct of claim 5.

11. A method for isolating a polypeptide encoded by the polynucleotide of claim 1 comprising isolating the polypeptide from a cell transformed with the polynucleotide.

* * * * *